United States Patent [19]

Kiyasu et al.

[11] Patent Number: 4,910,757
[45] Date of Patent: Mar. 20, 1990

[54] METHOD AND APPARATUS FOR X-RAY IMAGING

[75] Inventors: Senya Kiyasu; Takanori Ninomiya, both of Yokohama, Japan

[73] Assignee: Hitachi, Ltd., Tokyo, Japan

[21] Appl. No.: 266,369

[22] Filed: Nov. 2, 1988

[30] Foreign Application Priority Data

Nov. 6, 1987 [JP] Japan ................. 62-279240
May 30, 1988 [JP] Japan ................. 63-130108

[51] Int. Cl.[4] .................................. G01N 23/04
[52] U.S. Cl. .................................. 378/53; 378/157; 378/58
[58] Field of Search ................. 378/53, 157, 58

[56] References Cited

U.S. PATENT DOCUMENTS 3,848,130  11/1974  Macovski ........................ 378/53
3,944,830  3/1976   Dessing ........................... 378/53
3,974,386  8/1976   Mistretta ........................ 378/157

OTHER PUBLICATIONS

IEEE Trans. Nucl. Sci. NS-27, No. 2, (1980), pp. 961-968. (Provided in English).

Primary Examiner—Craig E. Church
Attorney, Agent, or Firm—Fay, Sharpe, Beall, Fagan, Minnich & McKee

[57] ABSTRACT

Two X-ray transmission images of an object, e.g. an electronic device package structure having plural soldering layers are detected in two directions inclined to the plural layers, on the basis of a relative position relation between both X-ray transmission images, one X-ray transmission image is converted on the assumption that soldering portions to be detected are located at a certain layer, into the image in the direction in which the other X-ray transmission image has been detected, and the converted X-ray transmission image is with the other X-ray transmission image to decide that the soldering portions at coincided positions are located at the layer at issue. Further, an object such as an electronic device package structure having soldering portions is irradiated with plural kinds of X-rays with different photon energy spectra to detect the corresponding X-ray transmission images of the object and the X-ray transmission images are processed referring to a previously prepared numerical value table indicating relations between the transmission distances of the plural kinds of X-rays for the soldering portions of the other substance and the transmission X-ray intensities therefor in order to separately detect an image of the soldering portions.

6 Claims, 17 Drawing Sheets

METHOD AND APPARATUS FOR X-RAY IMAGING

BACKGROUND OF THE INVENTION

The present invention relates to an X-ray imaging method and device for observing or testing an object having a plurality of layers, more particularly, a package structure of an electronic device having a plurality of soldering layers by detecting an X-ray transmission image thereof.

A transmission image of an object can be commonly obtained by irradiating the object with an electromagnetic wave such as an X-ray or a particle beam such as an α-ray and β-ray and detecting the transmission intensity thereof. The X-ray image is a typical example of such a transmission image.

Such a transmission image had a disadvantage that when a plurality of objects are superposed, it is frequently difficult to decide the front-rear relation thereof by the human eye. In order to obviate this disadvantage, a technique of separately detecting the respective objects with respect to differences among their depths by applying the depth information extraction technique by binocular vision to the X-ray transmission image has been proposed in the Proceedings of the 24th Annual Conference of the Society of Instrument and Control Engineers (1985) pp. 845–846.

The above binocular vision is a technique in which an object image is detected from two points apart from each other by a certain distance and the distance to the object is detected from the parallaxes of the image from the two directions.

In the prior art, as shown in FIG. 1, first, a group of objects are rotated by a minute angle $\Delta\theta$ around the axis. The rotation axis perpendicular to the transmission direction and two transmission images before the rotation and after the rotation are detected. This corresponds the objects that are binocularly visioned as shown in FIG. 2. It is understood from the comparison of two transmission images that the respective objects are shifted by minute amounts corresponding to their depths in the transmission angle. Therefore, the depth information of the respective objects can be obtained from the differences in the shift amounts.

More specifically, the depth amount h(x) in the above prior art is calculated as follows.

Both transmission images $f_1(x)$ and $f_2(x)$ can be approximated as $$f_1(x) = f\left(x - \frac{h(x)}{H}\left(\frac{D}{2} + x\right)\right) \quad (1)$$

$$\approx f(x) - \frac{h(x)}{H}\left(\frac{D}{2} + x\right)f_x(x)$$

$$f_2(x) = f\left(x + \frac{h(x)}{H}\left(\frac{D}{2} - x\right)\right) \quad (2)$$

$$\approx f(x) + \frac{h(x)}{H}\left(\frac{D}{2} + x\right)f_x(x)$$

where
$D = H \sin\Delta\theta$
H: distance between the said axis and the position of the detecting device Taking a difference between $f_1(x)$ and $f_2(x)$, $$f_2(x) - f_1(x) = f_{2-1}^{\Delta}(x) = \frac{D}{H} h(x)f_x(x) \quad (3)$$

Assuming that the spacial change in h(x) is smooth and the size of the object is negligibly smaller than the distance H, the differentiation in the x-direction is $$f_x(x) \approx \frac{1}{2} \frac{\partial}{\partial x}(f_1(x) + f_2(x)) \quad (4)$$

Thus, h(x) is obtained and so the depth information is obtained from the the transmission images.

In this way, the prior ar extracts the depth information from two detected transmission images of objects rotated by a minute angle $\Delta\theta$ and separately judges the objects by the differences in depth. In this method, in the approximation of equations (1) and (2), it is assumed that $$\frac{h(x) \cdot \sin \Delta\theta}{x} << 1 \quad (5)$$

Therefore, as the size of an object is smaller with respect to the depth amount h(x), the rotation angle $\Delta\theta$ must be as so sufficiently reduced. However, as $\Delta\theta$ becomes small, the difference between $f_1(x)$ and $f_2(x)$, i.e. the value of equation (3) becomes also small. This means that the accuracy in the depth amount h(x) obtained by equation (3) is reduced. Accordingly, the above prior art has an advantage that the method thereof is not applicable unless the size of an object is sufficiently larger than the depth amount to be detected.

Another prior art will be explained below. An X-ray transmission image is obtained by irradiating an object with X-rays and two-dimensionally detecting the intensity of the detected X-rays. Commonly the detection is carried out by directly taking the X-ray image on a film or indirectly taking the fluorescence emitted when the X-rays fall onto a fluorescent plate. The detection is also performed by converting the X-ray image into an optical image using an image intensifier and taking the optical image by e.g. a television camera to be detected as electrical signals.

The X-ray transmission image permits the part directly invisible from the outside to be detected. However, if substances are three-dimensionally superposed, all the substances are superposedly detected on the same image, so that it was frequently difficult to discrimintte the superposed portions from only the transmission image. There has been proposed in JP-A-57-61937 a method of detecting X-ray images using plural X-rays with different photon energies and processing these images to extract an image of a particular portion, thereby making it easy to observe the superposed substances. This method will be explained briefly.

Now, the model as shown in FIG. 3 is taken for X-ray transmission. It is assumed that an object consisting of a substance X 59 having a thickness of X and a substance Y 60 having a thickness of y which are superposed is irradiated with an X-ray e having an intensity $I_e$ and an X-ray f having an intensity of $I_f$ and the transmission X-ray intensities $I_e$ and $I_f$ are obtained. The X-ray e and the X-ray f are two X-rays with different photon energies. Further, it is assumed that the X-rays having a single wavelength are irradiated, and the X-ray absorption coefficients of substance X 59 and substance Y 60 for the X-ray e are $\mu_{Xe}$ and $\mu_{Ye}$, and likewise the X-ray absorption coefficients of substance X 59 and substance Y 60 for the x-ray f are $\mu_{Xf}$ and $\mu_{Yf}$. FIG. 4 is a graph showing the relation between the X-ray absorption coefficient and Y-ray photon energy for lead (Pb) and tungsten (W). If the substance X 59 is lead and the substance Y 60 is tungsten while the X-ray e and the X-ray f are shown as FIG. 4, $\mu_{Xe}$, $\mu_{Xf}$, $\mu_{Ye}$ and $\mu_{Yf}$ are different constants as shown in FIG. 4.

Then, the following equations hold.

$$I_e = I_o \exp(-\mu_{Xe} x - \mu_{Ye} y) \quad (6)$$

$$I_f = I_o \exp(-\mu_{Xf} x - \mu_{Yf} y) \quad (7)$$

Solving these equations with respect to x, $$x = \frac{\mu_{Yf} \ln\left(\frac{I_e}{I_o}\right) - \mu_{Ye} \ln\left(\frac{I_f}{I_o}\right)}{\mu_{Ye} \mu_{Xf} - \mu_{Yf} \mu_{Xe}} \quad (8)$$

This value indicates the thickness of the substance X. Therefore, if two X-ray transmission mmages are detected by using the X-ray e and the X-ray f and the above computations are carried out for all the corresponding points, an image indicative of the thickness of only the substance X 59 can be detected.

Now it should be noted in the above prior art that the irradiation of the X-ray with a single wavelength (monochromatic X-ray) is assumed, and so the change of the quality of the X-ray which will occur when the X-ray is transmitted through a substance has been neglected. However, it is difficult to use the monochromatic X-ray in actually detecting X-ray transmission images, and the irradiated X-ray has a photon energy spectrum which is continuous in a certain range. Then, the X-ray changes in its quality when it is transmitted through the substance so that equations (6) and (7) in which the X-ray absorption coefficients are assumed to be constant do not hold. Even if the thickness is obtained from equation (8), it will contain an error.

Further, a method for describing X in equation (8) using higher degree polynominals with respect to the terms of $I_n (I_e/I_o)$ and $I_n (I_f/I_o)$ but not by linea expressions has been proposed in IEEE Trans. Nucl. Sci. NS-27, No. 2 (1980) pp 961-968. However, this method, which performs an approximation by secondary or third order polynominals, does not also provide the result with high accuracy if non-linearity of X concerning each of $I_n (I_e/I_o)$ and $I_n (I_f/I_o)$ is too great.

SUMMARY OF THE INVENTION

A primary object of the present invention is to provide an X-ray imaging method and device which is capable of discriminating the respective layers e.g. soldering portions of the package structure of an electronic device from the respective parts of an X-ray transmission image regardless of the size of the package structure and at a high speed, thereby easily testing the layer parts.

Another object of the present invention is to provide an X-ray imaging method and device which is capable of separately detecting, with a high accuracy, an image of a certain substance such as a soldering portion from an X-ray transmission image of an object consisting of plural superposed substances, thereby testing that substance with a high accuracy.

$I_n$ order to attain the primary object, the present invention positively uses the information of the rough location of an object layer to be detected. More specifically, the information of the object layer to be detected is extracted as follows.

(1) A package structure of an electronic device having a soldering portion consisting of plural layers is rotated by a certain angle $\Delta\theta$ around the axis perpendicular to the layers, and two transmission images $f(\theta_1)$ and $f(\theta_2)$ are detected from two directions.

(2) Assuming that all the objects are located at a certain layer, an image $f'(\theta_1)$ before the rotation of $\Delta\theta$ is obtained from $f(\theta_2)$.

(3) $f(\theta_1)$ is compared with $f'(\theta_1)$ and the coincided portions are extracted.

(4) The extracted portions are decided to be located at the assumed layer.

(5) The procedures of (3) to (5) are repeated for a different layer and the layers where the respective parts are located are decided.

In order to attain another object of the present invention, the following procedures are carried out.

(1) By adjusting the tube voltage of an X-ray tube emitting X-rays and inserting a filter into the X-rays, the photon energy spectrum of an X-ray to be irradiated is changed, an the X-rays are irradiated to detect plural X-ray transmission images.

(2) When the respective transmission X-ray intensities are detected by radiating plural X-rays with different energy spectra, how they correspond to the transmission distances in a specific substance in an object are previously obtained for a set of the detected values. And the corresponding relations thereof are previously recorded on a numerical table.

(3) The X-ray transmission distances of the specific substance corresponding to the set of the detected values actually obtained through the plural X-rays are computed referring to the numerical table.

(4) The procedure of (3) is carried out for all the points of the detected X-ray transmission images thereby to separately detect the image indicative of the thickness of the specific substance.

Namely, the key point for attaining another object of the present invention is to previously prepare a numerical table indicating the relations between the intensities and the transmission distances of the transmitted X-rays. In this case, if these relations on the table are taken as fine as possible, the detection accuracy can be sufficiently enhanced. Therefore, by preparing table including the numerical values correctly corresponding to actual phenomena considering that the quality of an X-ray will change when it is transmitted through a substance, an error due to the change of the X-ray quality can be eliminated.

DESCRIPTION OF THE PREFERRED EMBODIMENTS

The present invention will be explained hereinafter with reference to the drawings.

Figure 7:
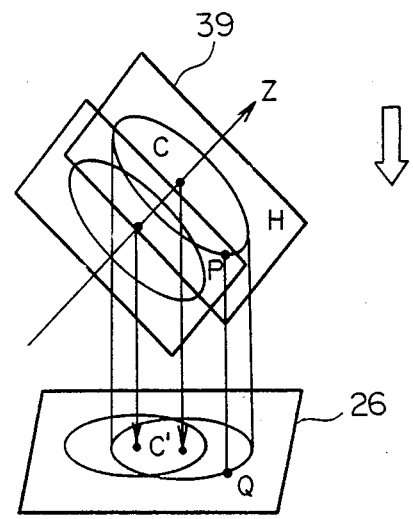
FIG. 7 is a view for explaining the principle of the present invention.
Figure 6:
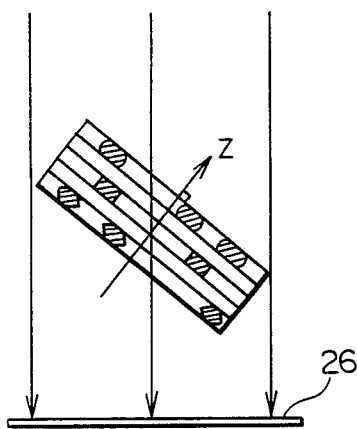
FIG. 6 is a view showing the direction of X-ray transmission for a package structure of an electronic device having a multi-layer structure.

First, a principle of layer discrimination in an X-ray transmission image in accordance with the present invention will be explained. Now, assumed is the case where the X-ray transmission image of an electronic device package structure (circuit board) having a multi-layer structure as shown in FIG. 9 is detected by means of parallel X-rays (beams) irradiated from the direction not perpendicular to that of the multi-layer as shown in FIG. 6. This method is also applicable to the X-ray transmission image by means of X-ray cone beams radiated from a point X-ray source. Now, it is assumed that an object is rotated around the Z-axis taken perpendicularly to the layers. Then, as shown in FIG. 7, a certain point P of the object moves to draw a circle on a plane H perpendicular to the rotary axis. Also, a point Q on the X-ray transmission image corresponding to the point P moves to draw an ellipse having a center point C' as shown n FIG. 7. If the parallel beams are used, the point C' is a point on the X-ray transmission image corresponding to a point C where the rotary axis intersects the plane H. Therefore, all the points on the same plane H move on the X-ray transmission image to draw the corresponding ellipses having the same center point C'. However, if the Z coordinate of the plane H shifts, the point C' also shifts as shown in FIG. 7. Therefore, the moving direction and distance of the point Q on the X-ray transmission image due to the rotation depends on the value of Z coordinate of the plane H on which the point P is located.

On the basis of the above principle, in the present invention, two X-ray transmission images of an electronic device package structure (circuit board) 3 obtained by rotating it by an angle $\Delta\theta$ are detected and compared with each other to carry out layer discrimination at the soldering portion. In accordance with the above principle, if the movement of a certain object on the X-ray transmission image can be detected from $f(\theta_1)$ and $f(\theta_2)$, the layer discrimination at the object can be made. However, it is difficult to detect the movement by finding out the corresponding objects between the two X-ray images. For this reason, the present invention uses the fact that in the electronic device package structure 3 having a multi-layer structure, the location of the portion (soldering portion) to be detected is limited to several known layers having a certain width.

If a certain layer X in the electronic device package structure 3 is noticed, the movement of any point in that layer on the X-ray transmission image can be predicted. Therefore, if any portion (soldering portion) to be detected is located at only the layer X, the image $f(\theta_2)$ can be obtained by elliptically rotating all the picture elements of the image $f(\theta_1)$ in accordance with the above prediction. Likewise, $f(\theta_1)$ can be obtained by elliptically rotating $f(\theta_2)$ in the reverse direction. Therefore, one of the X-ray transmission images before and after the rotation of $\Delta\theta$ can be obtained from the other.

Figure 8:
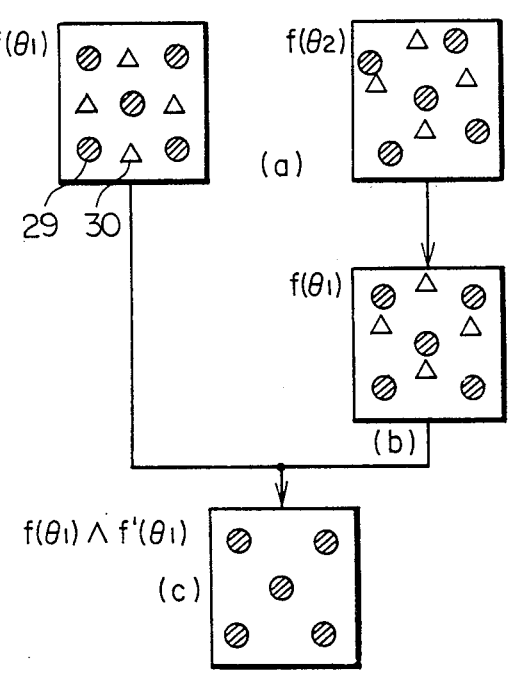
FIG. 8 is a schematic view of the X-ray transmission image obtained on the basis of the principle shown in FIG. 7.

Now, this fact is utilized. More specifically, first, $f(\theta_2)$ is rotated so as to coincide with $f(\theta_1)$ for the layer X. Thus, $f'(\theta_1)$ is obtained. This procedure means that the image before the rotation of $\Delta\theta$ is obtained assuming that the portions (soldering portion) to be detected are located at only the layer X (FIG. 8(b)). As seen from the comparison between $f(\theta_1)$ and $f(\theta_2)$, the portions 29 located at the layer X coincide in both images. However, since the images $f(\theta_1)$ and $f(\theta_2)$ include the images of the portions 30 located at the layer other than the layer X, those portions do not coincide. As shown in FIG. 8(c), by extracting the coincided portions, the portions 29 located at the layer X can be extracted from $f(\theta_1)$. If the above procedure is carried out successively for all the layers, the portions located at each layer can be individually extracted.

The present invention will be more concretely explained in connection with the embodiment shown in the drawings.

Figure 1:
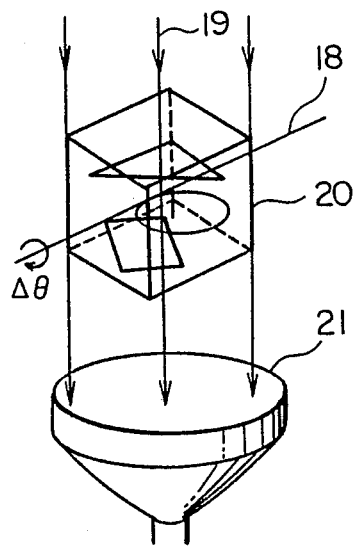
FIG. 1 is a perspective view showing a method of detecting a transmission image used in the prior art binocular vision technique.
Figure 2:
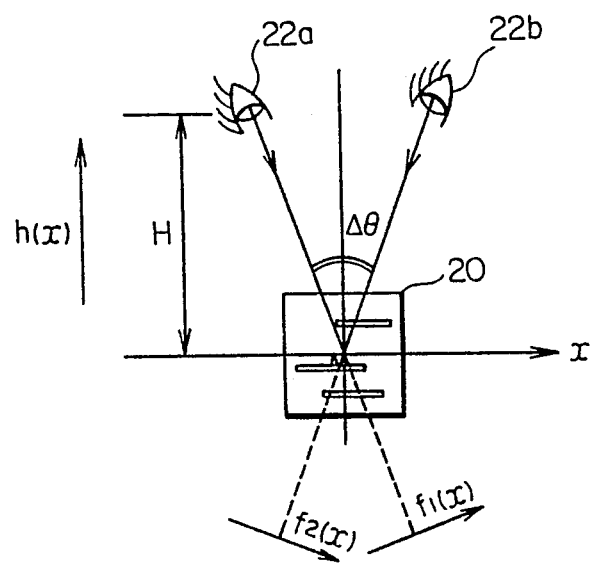
FIG. 2 is a view for explaining the principle of the binocular vision technique.
Figure 3:
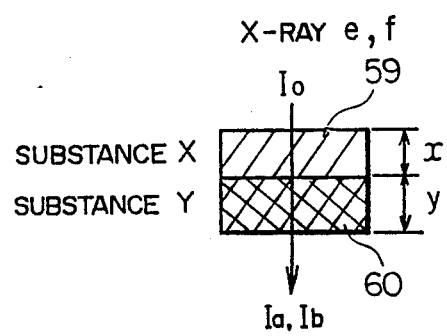
FIG. 3 is a view showing one model for explaining X-ray transmission.
Figure 4:
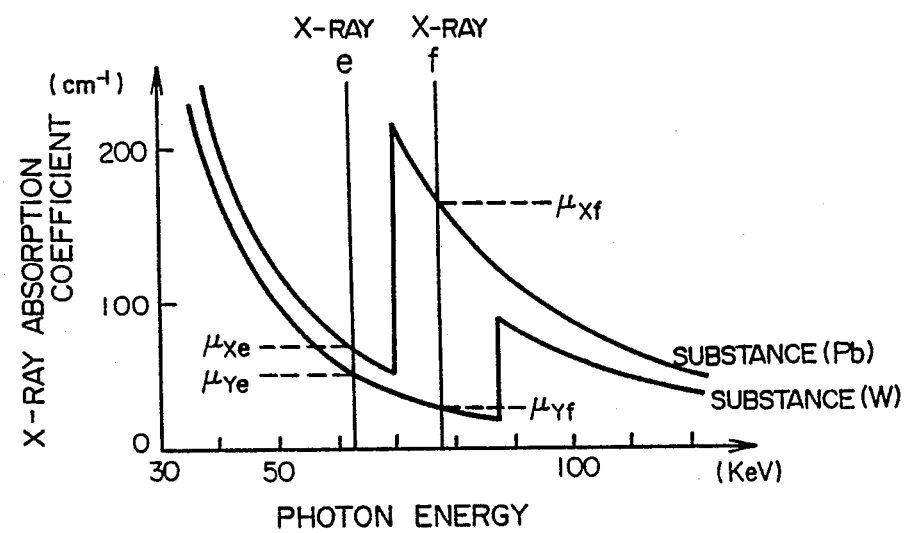
FIG. 4 is a graph showing known relations between the X-ray absorption coefficient and the photon energy of the radiated X-ray in lead (Pb) and tungsten (w)
Figure 5:
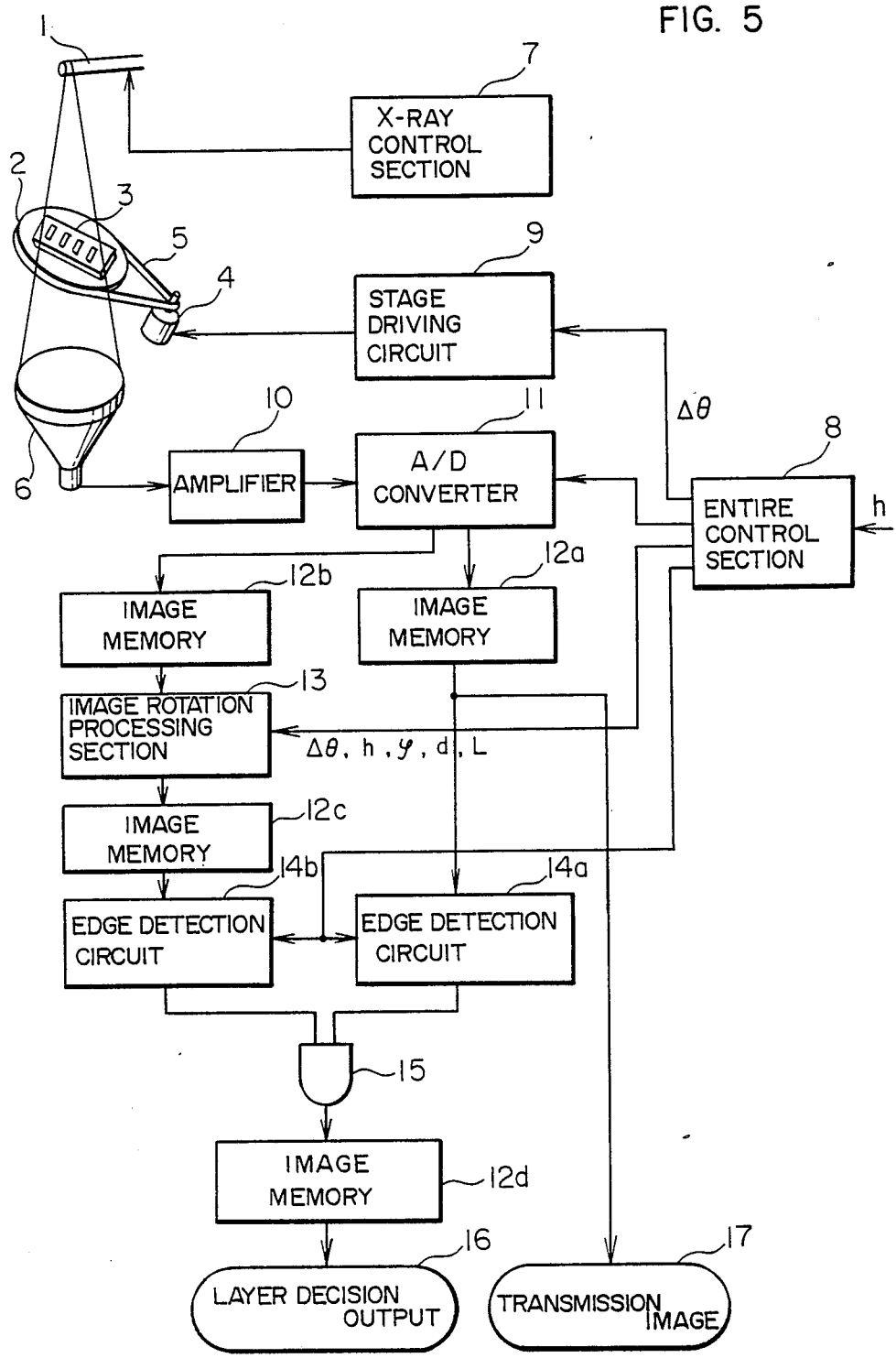
FIG. 5 is a schematic block diagram showing one embodiment of a device for detecting a soldering portion of an electronic device using an X-ray transmission image according to the present invention.

FIG. 5 shows one embodiment of a device for performing layer discrimination in accordance with the present invention. This embodiment is suitable to perform, by means of X-ray images, the observation and the defect detection of a soldering portion in an electronic device package structure (circuit board) having a multi-layer structure, such as a both-side packaging board. 1 is an X-ray source; 2 is a $\theta$ (rotation) stage on which a circuit board 3 having a multi-layer structure is placed; 4 is a motor for rotating the $\theta$ stage 2; 5 is a rubber belt for transfer the rotating power of the motor 4 to the $\theta$ stage 2; 6 is an image intensifier for taking a X-ray transmission image; 7 is an entire control section which orders $\Delta\theta$, h, etc. and also produces a synchronization signal; 9 is a stage driving circuit for driving the motor 4 so as to drive the $\theta$ stage; 10 is an amplifier for amplifying the image signal obtained from the image intensifier; and 11 is an A/D converter for converting the image signal obtained from the amplifier 10 into a multi-value signal.

Figure 9A:
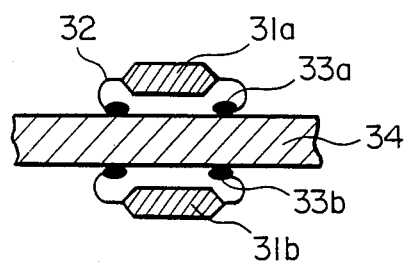
FIG. 9(a,b) is a longitudinal sectional view of one example of a electronic device package structure (circuit board) to which the present invention is applied.
Figure 9B:
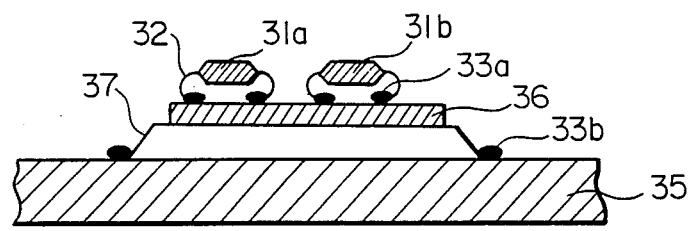

The board 3 to be detected in this embodiment may be a two-sided package board (electronic device package structure) the section of which is shown in FIG. 9A or a circuit board (electronic device package structure) having plural layers such as soldering layer, the section of which is shown in FIG. 9B. In the electronic device package structure as shown in FIG. 9A, IC lead wires 32 of IC's 31a and 31b are connected with a two-sided side printing board 34 through soldering portions 33a and 33b, respectively. In the case where the IC's 31a and 31b are packaged (or mounted) at the symmetrical positions on both sides of the board, if the X-ray images are to be detected from the direction perpendicular to the board 34, the soldering portions 33a and 33b on both sides will be superposedly detected so they can not be discriminated. Therefore, in this case, it is indispensable to set the X-ray transmission direction at the direction inclined from above to the board. In the electronic device package structure as shown in FIG. 9B, IC lead wires 32 of IC's 31a and 31b are connected with a printing board 36 through soldering portion 33a, and board lead wires 37 are connected with a printing board 35 through soldering portions 33b. The soldering portions 33a and 33b are located at up and down two layers. This embodiment intends to, in detecting the X-ray transmission image of the board to be tested, decide or discriminate at which side of the two-sided board (FIG. 9A) the respective soldering portions on the image are located or at which layer of the multi-layer board (FIG. 9B) they are located (hereinafter referred to "layer discrimination").

In operation, the board 3 to be tested is placed on the $\theta$ stage 2 that can be rotated by the motor 4 and is irradiated with X-rays from the X-ray source 1 provided above the $\theta$ stage. The energy and dose of the X-ray can be changed in the X-ray control section 7 by adjusting the X-ray generating voltage and current. The inclined angle $\phi$ of the $\theta$ stage 2 is no required to be fixed, but its value must be always supplied to an image rotation processing section. The flow of the X-ray image detection and of the layer discrimination processing is controlled by an entire control section 8. The entire control section 8 is constituted by a microcomputer which contains a memory in which the whole control procedure is programmed. The X-ray having permeated through the board 3 is detected by the image intensifier 6 and the image signal thus obtained is amplified by the amplifier 10. Under the control of the entire control section 8, the amplified image signal is converted into a digital (multi-value) signal by the A/D converter 11, which is in turn stored in the image memory 12a as a multi-value image. Next, the $\theta$ stage 2 is rotated by an angle $\Delta\theta$ by driving the motor 4 through the stage driving circuit 9 under the control of the entire control section 18. Then, an X-ray transmission image is stored in the image memory 12b in the same manner. Thus, the X-ray transmission images $f(\theta_1)$ and $f(\theta_2)$ detected in two directions are provided. ($\theta_2=\theta_1+\Delta\theta$) Thereafter, the image rotation processing section 13 is actuated by the entire control section 18. Then, the respective picture elements of the image $f(\theta_2)$ stored in the image memory 12b are rotated for a specific layer to be discriminated (by specifying h which is the value of $Z_S$ coordinate of the specific layer) to be converted into the corresponding picture elements at the position before the rotation of $\Delta\theta$, which are in turn stored in the image memory 12C. The image rotation processing section 13 is constituted by a microcomputer for performing processings and a memory in which the processing procedure is stored. This section may be replaced by the microcomputer and the program memory which constitute the entire control section 8.

Figure 10:
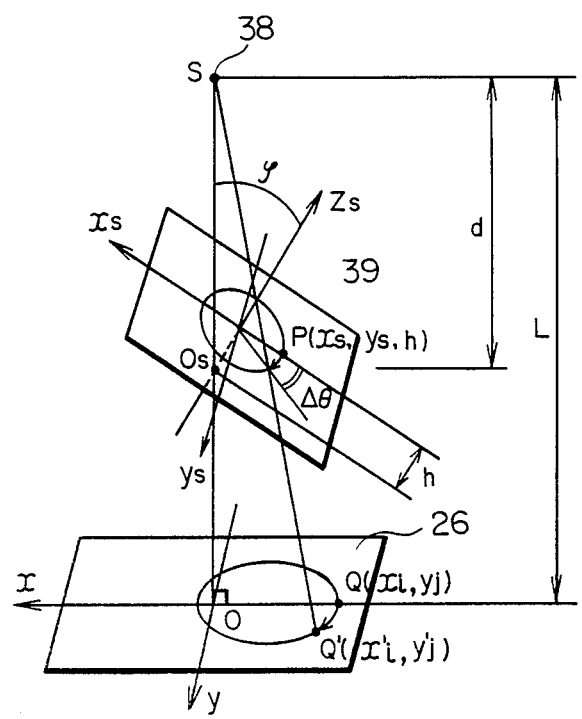
FIG. 10 is a view for explaining the manner of setting a coordinate system in the image rotation processing which is performed in an image rotation processing section in FIG. 5.

The concrete processings performed by the image rotation processing section 3 are as follows. The coordinates for the imaging plane on which the X-ray transmission images are detected by the image intensifier 6 and the later plane 39 in parallel to the $\theta$-stage 2 are set as shown in FIG. 10. More specifically, the foot of a perpendicular line from the ray source S38 of the X-ray source 1 to the imaging plane 26 is set as an origin O of x-y coordinates and an origin $O_s$ of $x_S$-$y_S$-$z_S$ coordinates (an intersection of the $z_S$-axis and line SO) is located on a line connecting S and O. The rotating axis of the $\theta$-stage 2 coincides with the $Z_S$ axis. Now it is assumed in such a coordinate system that a certain point P ($x_s$, $y_s$, h) on a layer plane 39 having a $z_s$ coordinate of h in the $x_Sy_Sz_S$ space corresponds to a point Q ($x_i$, $y_j$) on the imaging plane 26. Assuming that the point Q moves to a point Q'($x'_i$, $y'_j$) when the $\theta$ stage 2 is rotated by $-\Delta\theta$ taking a counter-clockwise direction as a positive rotation direction, the convertion from the point Q to the point Q' can be expressed by the following equations $$\begin{pmatrix} x'_i \\ y'_j \end{pmatrix} = -L \begin{pmatrix} \dfrac{x_t \cos\phi - h\sin\phi}{x_t\sin\phi + h\cos\phi - d} \\ \dfrac{y_t}{x_t\sin\phi + h\cos\phi - d} \end{pmatrix} \quad (9)$$

where $$\begin{pmatrix} x_t \\ y_t \end{pmatrix} = \begin{pmatrix} \cos\Delta\theta & \sin\Delta\theta \\ -\sin\Delta\theta & \cos\Delta\theta \end{pmatrix} \left\{ \begin{pmatrix} d\sin\phi \\ 0 \end{pmatrix} + K\begin{pmatrix} x_i\cos\phi - L\sin\phi \\ y_j \end{pmatrix} \right\} \quad (10)$$

where

-continued $$K: \frac{d\cos\phi - h}{x_s\sin\phi + L\cos\phi},$$

$\phi$: an inclination angle of the $\theta$ stage,
d: distance from the X-ray source to the origin $O_s$ of the $\theta$ stage 2,
L: distance from the X-ray source to the origin O of the imaging plane 26.

L and d are previously determined. $\phi$ is predetermined if fixed or detected by a detector (not shown) if varied h which indicates a $z_s$ coordinate and so corresponds to the respective layer positions in the circuit board 3 is specified by successively changing it.

Figure 11A:
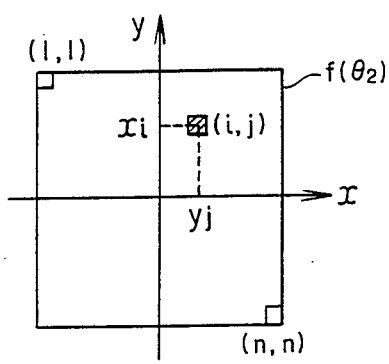
FIG. 11(a,b) is a view showing the relation between the image data $f(\theta_1)$ and $f'(\theta_1)$ and the coordinate system in the image rotation processing.

It is assumed that the image data stored in the image memory 12b is arranged in a two-dimensional array of n x n and corresponds to the imaging coordinate (x, y) as shown in FIG. 11. Then, the image f($\theta_2$) which is stored in the image memory 12b is converted into the previous image f'($\theta_1$) by rotating the image f($\theta_2$) by the angle of $\Delta\theta$ for the layer plane 39 of $z_s=h$ (using the layer plane 39 as a reference layer) in the image rotation processing section 13. ($\theta_1=\theta_2-\Delta\theta$) More specifically, the image rotation processing section 13, under the control of the entire control section 8, computes the coordinate (x'$_i$, y'$_j$) from the above conversion equation (9), (10) on the basis of $\Delta\theta$ and h (it is assumed that $\phi$, d and are predetermined) specified by successively varying the coordinate (x$_i$, y$_j$) which is an address of a picture element (i, j) of the image f($\theta_2$) on the image memory 12b (FIG. 11A). And the image rotation processing section 13 reads out the multi-value data of the picture element (i, j) stored at the address (x$_i$, y$_j$) on the image memory 12b and writes it on the picture element (i', j') at the address (x'$_i$, y'$_j$) on the image memory 12c.

Figure 11B:
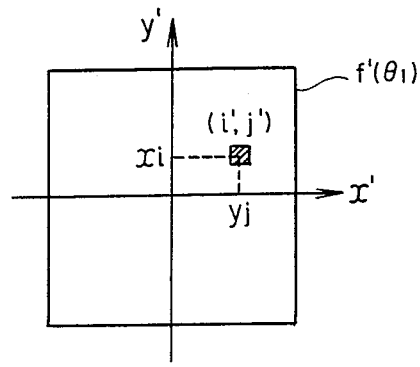

If the above processing is carried out for all the picture elements (i, j), the image f'($\theta_1$) will be stored in the image memory 12c (the picture elements (i', j') projected beyond the image range shown in FIG. 11B are neglected).

Finally, edge detection circuits 14a and 14b under the control of the entire control section 8, detect edges of the images f($\theta_1$) and f'($\theta_1$) stored in the image memories 12a and 12b, respectively. The edge detection is carried out in synchronization with each other between both images. The coincidence between the corresponding picture elements is immediately detected by an AND circuit 15 and is stored sequentially in an image memory 12d so as to form a binary image. Thus, the edge image of the soldering portion located at a specific layer corresponding to $z_s=h$ is obtained in the image memory 12d.

Figure 12:
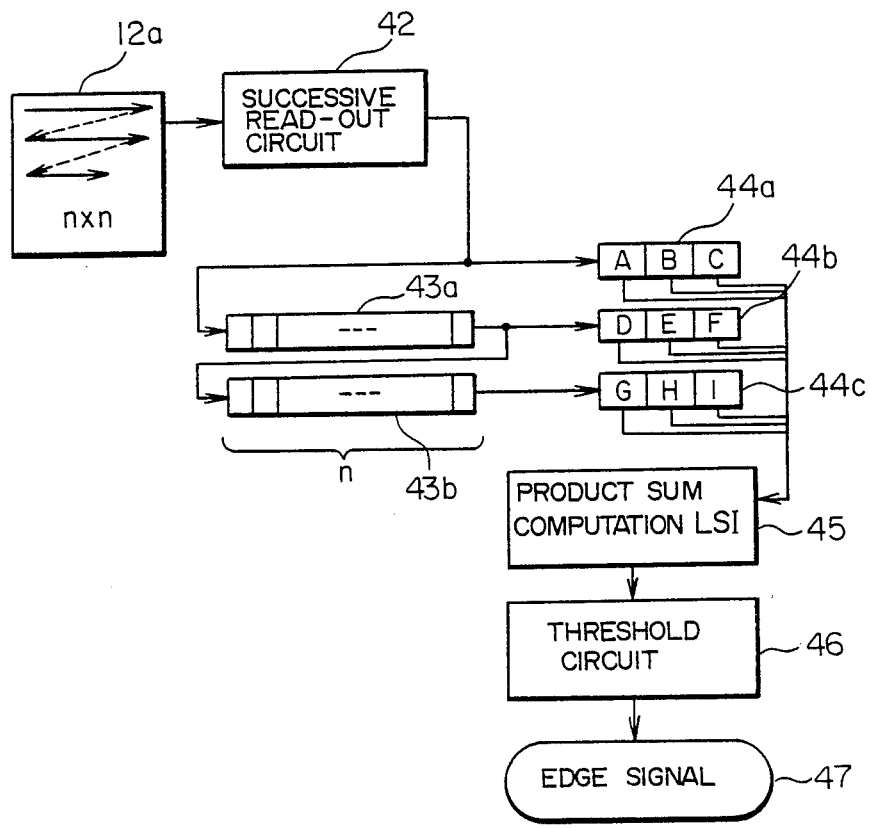
FIG. 12 is a block diagram of the concrete construction of the edge detection circuit of FIG. 5.

The edge detection circuits 14a (and 14b) may be constituted in a circuit arrangement as shown in FIG. 12. The multi-value image data is successively read out from the image memory 12a by a successive read-out circuit 42, and sent to shift registers 43a and 43b which are n stage shift registers. The shift registers 43a and 43b are connected to three stage registers 44a, 44b and 44c as shown in FIG. 12. Thus, the data of a certain 3×3 area on the image memory 12a are obtained at the regions A to I of the three-stage shift registers 44a, 44b and 44c. The values at the regions A to I are sent to a product-sum computation LSI45 in which the computation for edge detection is accomplished. For example, if a Laplacian is used as an edge detection operator, E×4-B-D-F-H may be computed. The computation result is sent to a threshold circuit 46. If the result is not less than a redetermined value, a signal of H is produced from the threshold circuit 46 whereas in other cases, a signal of L is produced.

Incidentally, in accordance with this embodiment, the coincidence detection of the corresponding picture elements may be carried out without storing an output of edge detection in the image memory so that the capacity of the image memory may be comparatively small.

Figure 13:
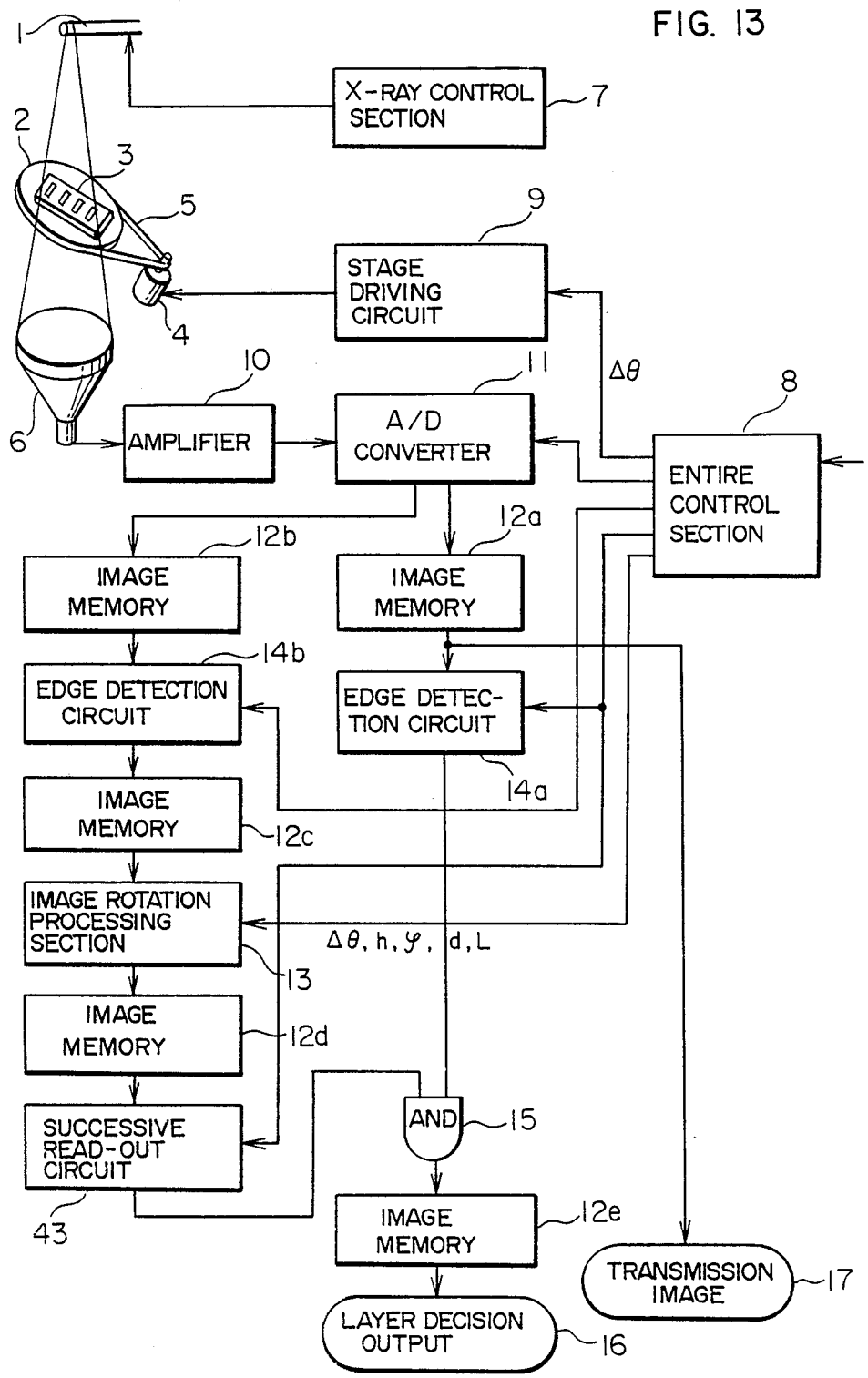
FIG. 13 is a schematic block diagram of another embodiment according to the present invention which is different from that of FIG. 5.

FIG. 13 shows a second embodiment of a device for carrying out the layer discrimination in accordance with the present invention. This embodiment is entirely the same as the first embodiment of FIG. 5 in the processings to the image memories 12a and 12b. Subsequently, in the firs embodiment, the image rotation processing is performed for the multi-value image and thereafter the edge detection is performed to extract the coincided edge images, thereby providing the result of layer discrimination. On the other hand, in this embodiment, the image stored in the image memory 12b is first subjected to the edge detection by the edge detection circuit 14b, thereby storing the edge image in the image memory 12c. The edge image which is a binary image is subjected to the image rotation processing, in the same manner as in the previous embodiment, by the image rotation processing section 13 on the basis of the commands such as $\Delta\theta$, h, etc. from the entire control section 8 and the result thereof is stored in the image memory 12d. Finally, each the picture elements successively read out by the successive read-out circuit 43 are subjected to the coincidence detection by the AND circuit 15 in the same manner as the previous embodiment to provide the result of layer discrimination. Since the image rotation processing by the image rotation processing section 13 is performed for the binary image, the processing speed can be enhanced.

Figure 14:
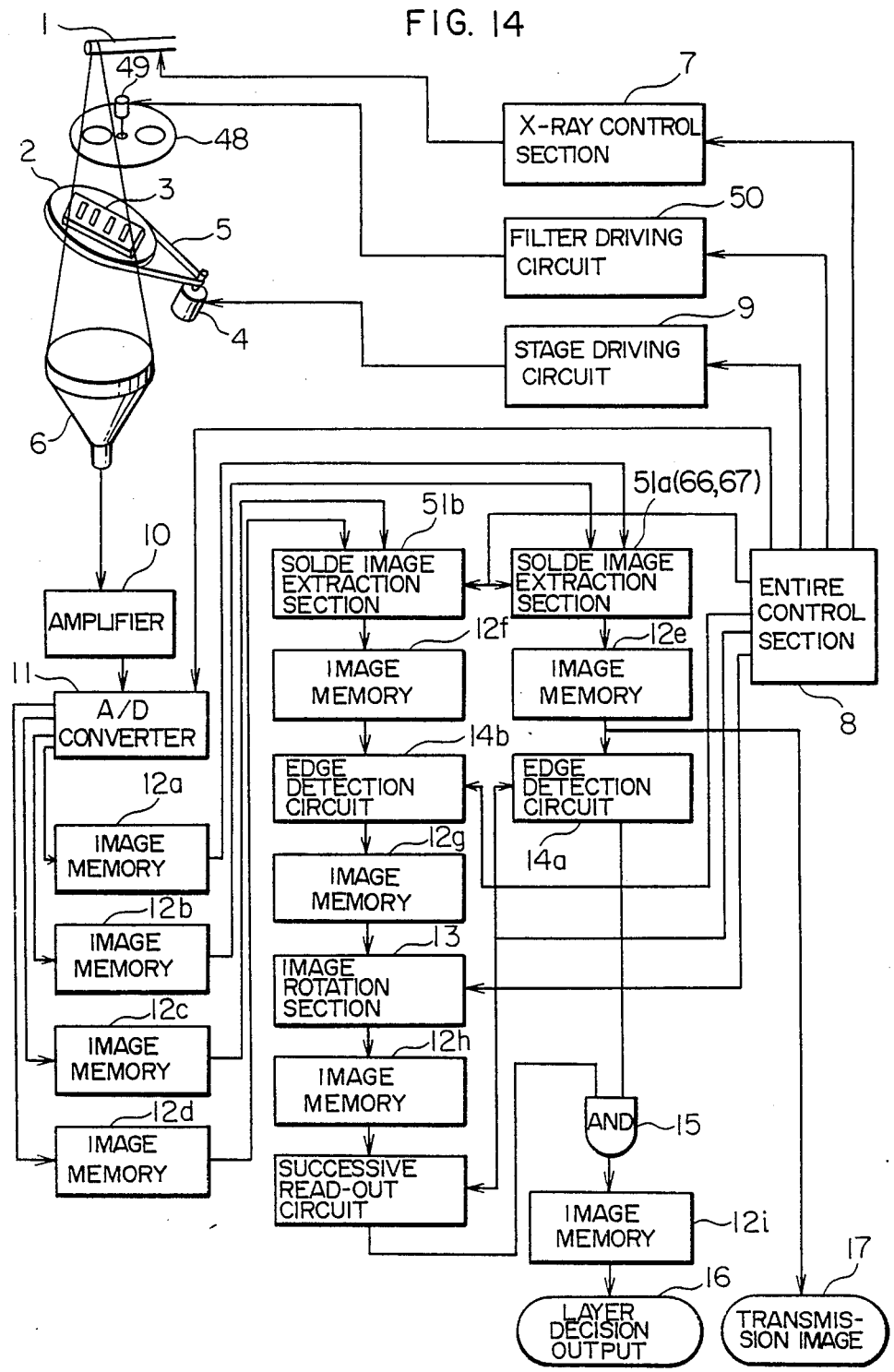
FIG. 14 is a schematic block diagram of still another embodiment according to the present invention which is different from that of FIG. 5.

FIG. 14 shows a third embodiment of a device for carrying out the layer discrimination in accordance with the present invention. This embodiment includes means for extracting only a solder image from the X-ray transmission image in addition to the embodiment of FIG. 13. Namely, this embodiment does not perform the layer discrimination directly using the X-ray image, but intends to once extract the solder image from the X-ray transmission image and to subject it to the same layer discrimination. This embodiment has an advantage that the soldering portion can be efficiently detected in the case where an object t be detected includes a substance having a high X-ray absorption coefficient as well as the solder, for example, lead wires of the circuit board are made of tungsten. The technique used in this embodiment is to reveal only the solder image using the difference in the absorption coefficient to X-rays. This technique itself is disclosed in the following. As shown in FIG. 14, a filter 49 is arranged between the X-ray source 1 and the $\theta$ stage so that copper plates having several thicknesses can be inserted on the X-ray radiation passage. The X-ray spectrum can be varied by adjusting the X-ray generating voltage and the thickness of the copper plate fitter. The wavelength of the irradiated X-ray is varied by an X-ray control section 7 and a filter driving circuit 50 which are controlled by the entire control section 8. The X-ray transmission images detected using the X-rays with different wavelengths are stored in the image memory 12a and 12b. These X-ray transmission images are processed in a solder image extraction section 51a (66, 67) to reveal only the solder image, and the result is stored in the image memory 12e. The solder image extraction sections 51a and 51b can be constituted by a microcomputer which contains a memory storing a programmed processing procedure. The processing procedure is described in the following. Likewise, the solder image obtained when the θ stage 2 is rotated by Δθ by the stage driving circuit 9 under the control of the entire control section 8 is extracted by the solder image extraction section 51b and stored in an image memory 12f. Thereafter, the same processing as in the second embodiment is carried out to provide a layer discrimination output.

As described above, in accordance with the present invention, by transmitting X-rays through an electronic device package structure having a multi-layer structure from the direction other than the direction perpendicular to the multi-layer structure, it can be decided at which layer the respective parts of the X-ray transmission images are actually located.

Embodiments of a device for separately detecting soldering portions in accordance with the present invention will be explained.

Figure 15:
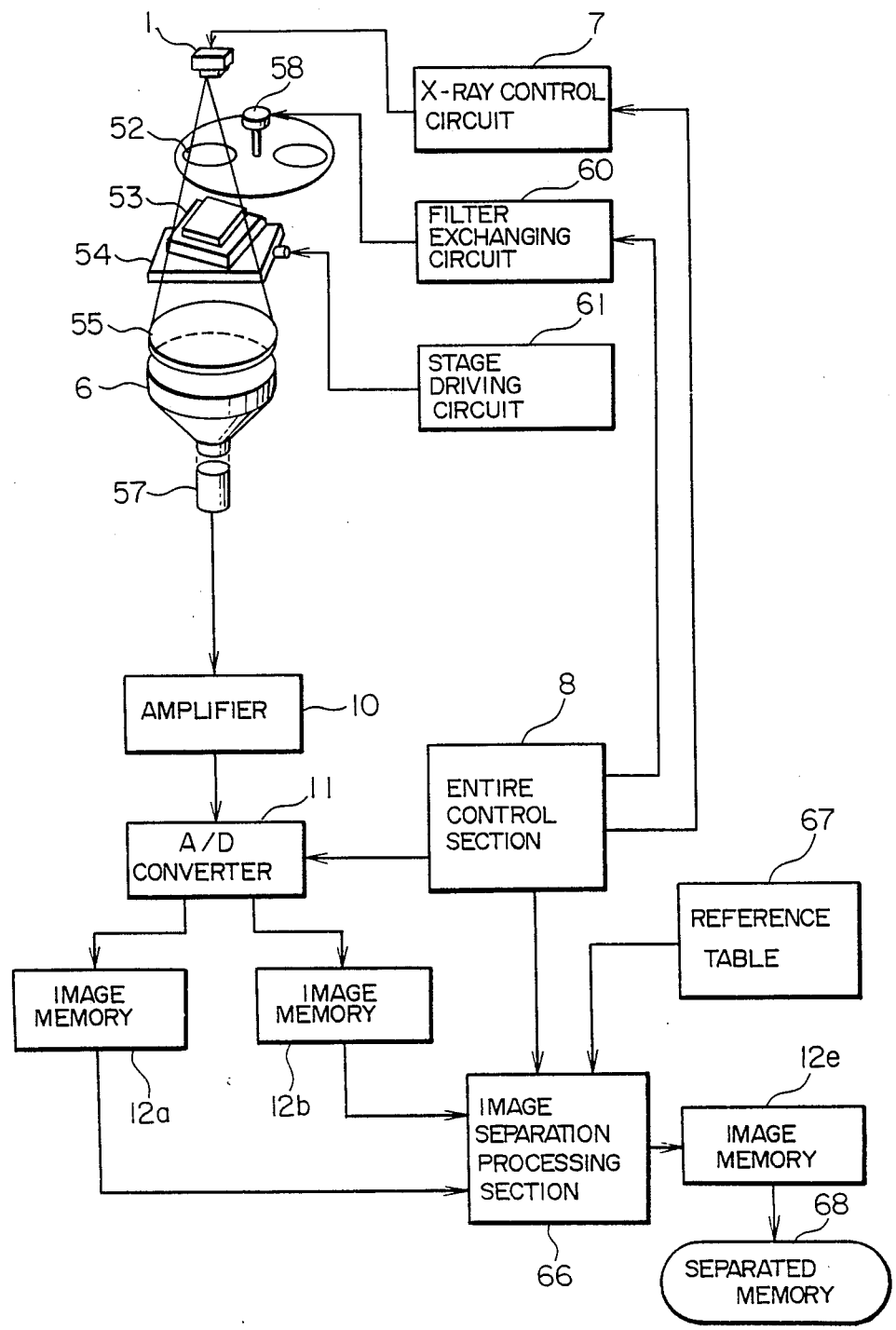
FIG. 15 is a schematic block diagram of an embodiment of the device for discriminating a soldering portion from the other portions according to the present invention.
Figure 16:
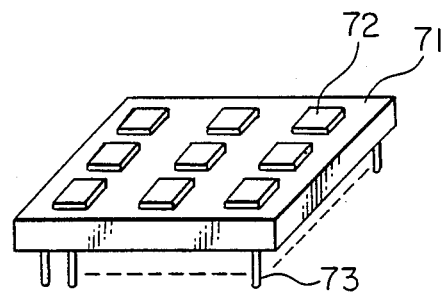
FIG. 16 is a perspective view of one example of an electronic device package structure (circuit board) to which the present invention is applied.
Figure 17:
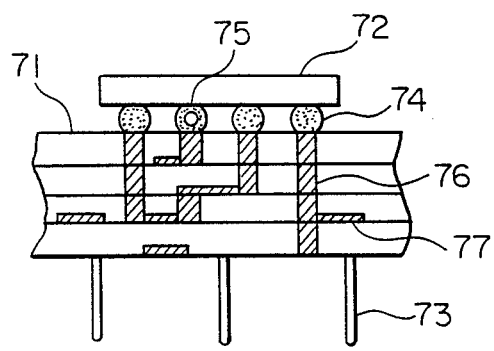
FIG. 17 is a sectional view of the structure of FIG. 16.
Figure 18:
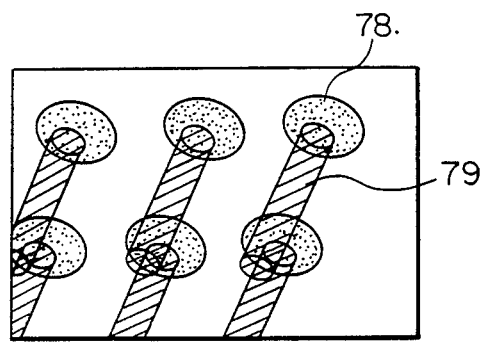
FIG. 18 is a schematic view f the X-ray transmission image of the structure shown in FIGS. 16 and 17.

FIG. 15 shows one embodiment of such a device. This embodiment is suitable, in the case where the lead wires in a circuit board are made of metal such as tungsten and soldering portions are located thereon, to separately detect the soldering portion image from the detected X-ray transmission image in which both images are superposed. FIG. 16 shows one example of the circuit board to be detected in its perspective view. FIG. 17 is a cross sectional view thereof. As seen from FIGS. 16 and 17, IC chips 22 are connected with a ceramic substrate 71 at minute soldering portions 74. The main composition of solder is mainly lead (Pb). There are, in the ceramic substrate 71, wiring patterns 77 in plural layers and through-holes 76 for connecting them (The wiring leads are made of tungsten (w) or molybdenum (Mo)). In the X-ray transmission image of this circuit board, one example of which is shown in FIG. 18, the images of the soldering portions 74 with larger X-ray attenuation and through-holes 76 are superposedly detected. Therefore, it is difficult to discriminate the images of the soldering portion and particularly difficult to recognize the shape defect such as a void 75 (FIG. 17) at the portion where the solder images 78 are superposed on through-hole images 79. This embodiment intends to separately detect the solder images for such a circuit board in order to efficiently observe or test the soldering portions.

As shown in FIG. 15, an object (circuit board) 53 to be detected is placed and positioned on a sample stage 54 which is driven by a stage driving circuit 61. The X-rays generated in the X-ray source 1 are irradiated to the object 53 through a filter 52. The X-ray source 1 of μ-focus type is advantageous to expansively detect a minute object. The photon energy spectrum of the irradiated X-rays is selected by the tube voltage which is adjusted by the X-ray control circuit and the filter 52 which is exchanged by a motor 58 driven by a filter exchanging circuit 60.

It is necessary to discriminate between the soldering image and the image of connecting lines as disclosed above. However, solder is mainly composed of lead while connecting lines are formed by tungsten metal or molybdenum metal. So, the following is explained by using lead and tungsten as examples.

Figure 19:
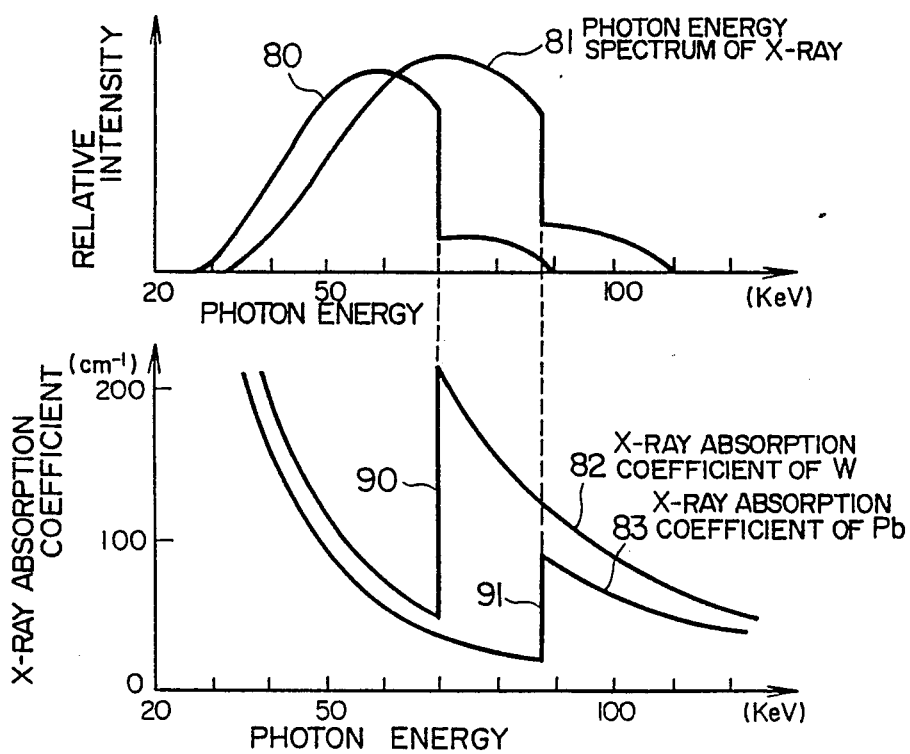
FIG. 19 is a graph showing the characteristics of the photon energy spectrum of the radiated X-ray and the X-ray absorption coefficient in lead (Pb) and tungsten (W)

FIG. 19 shows the photon energy spectra of X-ray when the tube voltage is 90 kV and the tungsten (w) plate filter used is 0.1 mm thick as 80 and the photon energy spectra of X-ray when the tube voltage is 110 kV and the lead (Pb) plate filter used is 0.2 mm thick as 81. FIG. 19 also shows the characteristics of the X-ray absorption coefficients of lead (83) and tungsten (82). The X-ray absorption coefficient of a substance has a discontinuous point called an absorption edge as shown in FIG. 19. n the case where the images of lead and tungsten are separated by using the difference between lead (solder) and tungsten (connecting lines) in X-ray absorption from the image of X-ray in which the images of lead (solder) and tungsten (connecting lines) are superposed, the detection using two X-rays having the photon energy before and after this absorption edge 90 and 91 produce the large difference in detected value. This is due to the fact that the large difference is produced between the absorption coefficient of tungsten and lead in the energy region from absorption edge 90 to 91, by irradiating X-ray having many photons with energy smaller than absorption edge 90 or X-ray having many photons with energy larger than absorption edge 91 and X-ray having many photons with energy between absorption edge 90 and 91. So, this method is profitable in increasing the processing precision of the separate detection.

By the way, a tungsten filter is used to get X-ray a having many photons with energy smaller than absorption edge 90. A lead filter is used to get X-ray b having many photons with energy between absorption edge 90 and 91. A copper filter etc. without absorption edge 91 is also used to get X-ray b instead of the lead filter. However, tee lead filter attains high sensitivity detection by separating the images of the solder and the connecting lines from the X-ray image as the absorption edge 91 of the lead filter makes the width of spectrum narrow.

For the reasons mentioned above, if the image of lead (Pb) or tungsten (w) is to be separately detected from the image of the object having Pb or w, it is advantageous to use a lead (Pb) plate filter if Pb is contained in the object and to use a tungsten (w) plate filter if tungsten is contained in the object. Thus, in this embodiment, the condition as mentioned above has been adopted to select two kinds of X-ray a (photon energy spectrum 80 of X-ray) and b (photon energy spectrum 81 of X-ray).

The procedure of detecting and processing the X-ray transmission image is controlled by the entire control section 8 which is constituted by a microcomputer in which the control procedure is programmed.

Figure 20:
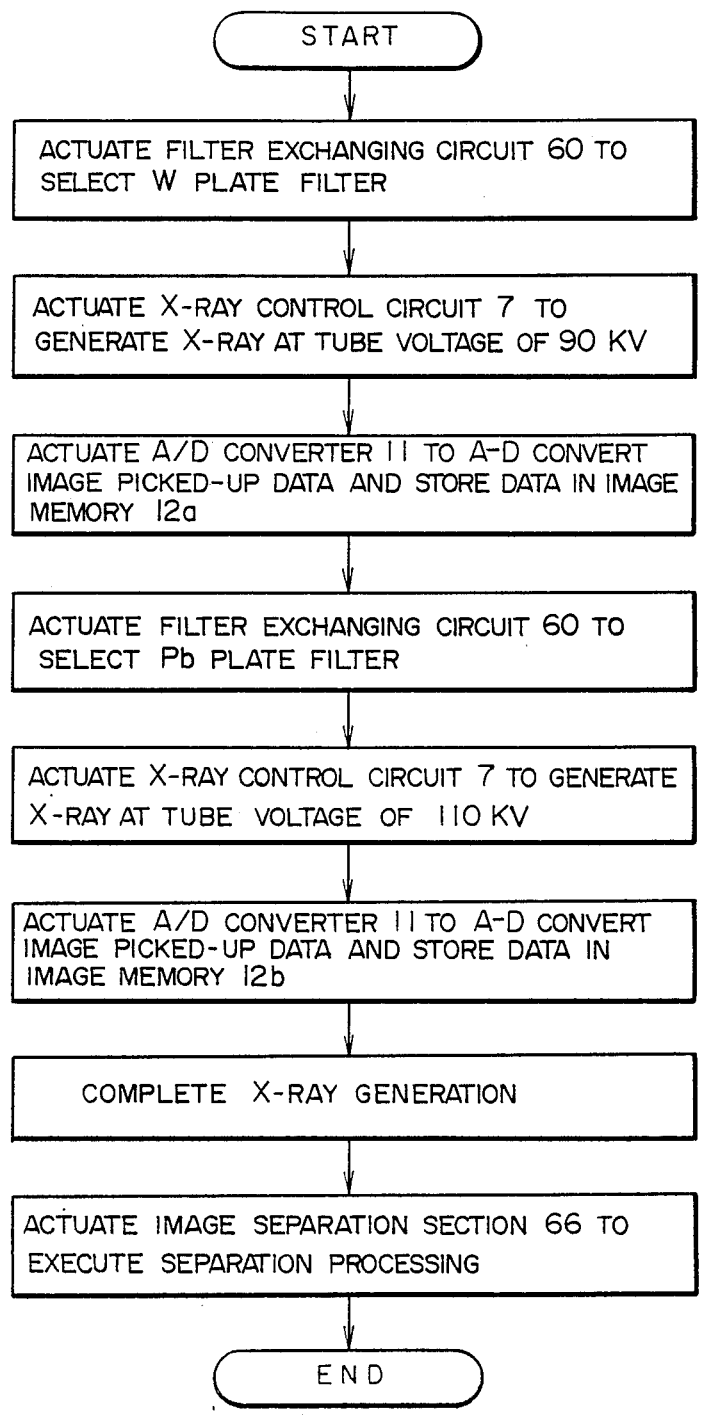
FIG. 20 is a flow chart showing the processing procedure performed in the entire control section of FIG. 15.

FIG. 20 shows a flowchart of the control procedure. First, the X-ray a (80) selected by the X-ray control circuit 7 and the filter exchanging circuit 60 under the control of the entire control circuit 8 is irradiated to the object 53 to be detected. The X-ray transmitted through the object 53, after its scattering X-ray has been eliminated, is detected as an image signal by a detection which is constituted by the image intensifier 6 and a television camera 57. The detected image signal is amplified by the amplifier 10 and A-D converted by the A/D converter 11 by a command sent from the entire control section 8. The thus obtained image is stored in the image memory 12a. The image detected using the X-ray b(81) in the same procedure is stored in the image memory 12b. Thereafter, image separation is performed by an image separation processing section 66 actuated by the entire control section 8. More specifically, the solder image is separated by the image separation section 66, which is constituted by a microcomputer having a programmed processing procedure, using a reference table 67 for the images stored in the image memories 12a and 12b. The image separation section 67 may share a microcomputer with the entire control section 8.

Figure 21:
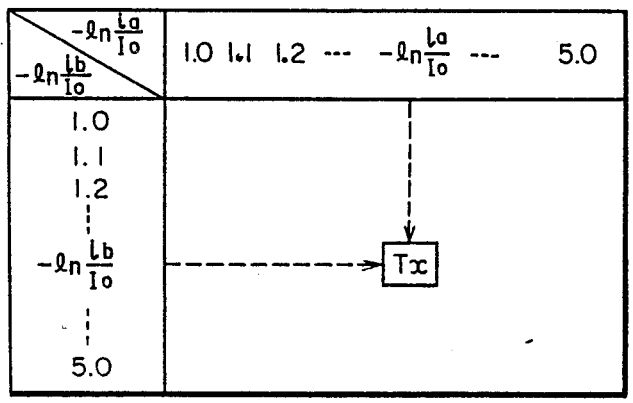
FIG. 21 is a view showing a numerical value table which represents the contents of a reference table shown in FIG. 15.

The processings carried out by the image separation processing section 66 will be explained. In the FIGS. 16 to 18, the material of solder is lead (Pb) and the material of through hlles is tungsten (w). It is assumed that the X-ray a(80) and X-ray b(81) with an intensity Io are irradiated, and the transmission X-ray intensities of Ia and Ib are obtained. Then, there is only one set of the thickness Tx of lead (Pb) and the thickness Ty of tungsten (w). Therefore, if the thickness Tx of Pb corresponding to several sets of Ia and Ib are previously obtained, the thickness Tx can be obtained from the detected transmission X-ray intensities of Ia and Ib. Thus, in order to record the value of Tx corresponding to a set of Ia and Ib, a numerical value table as shown in FIG. 21 is previously prepared. In this case, considering that Ia and Ib are exponentially attenuated for a transmission distance, the values of Tx corresponding to $-\ln(Ia/Io)$ and $-\ln(Ib/Io)$ taken for intervals of 0.1 from 1 to 5, for example, in order to enhance the detection precision are prepared. This numerical value table is previously stored in a reference table 67 constituted by a memory which can be read out by the microcomputer of the image separation processing section 66.

Figure 22:
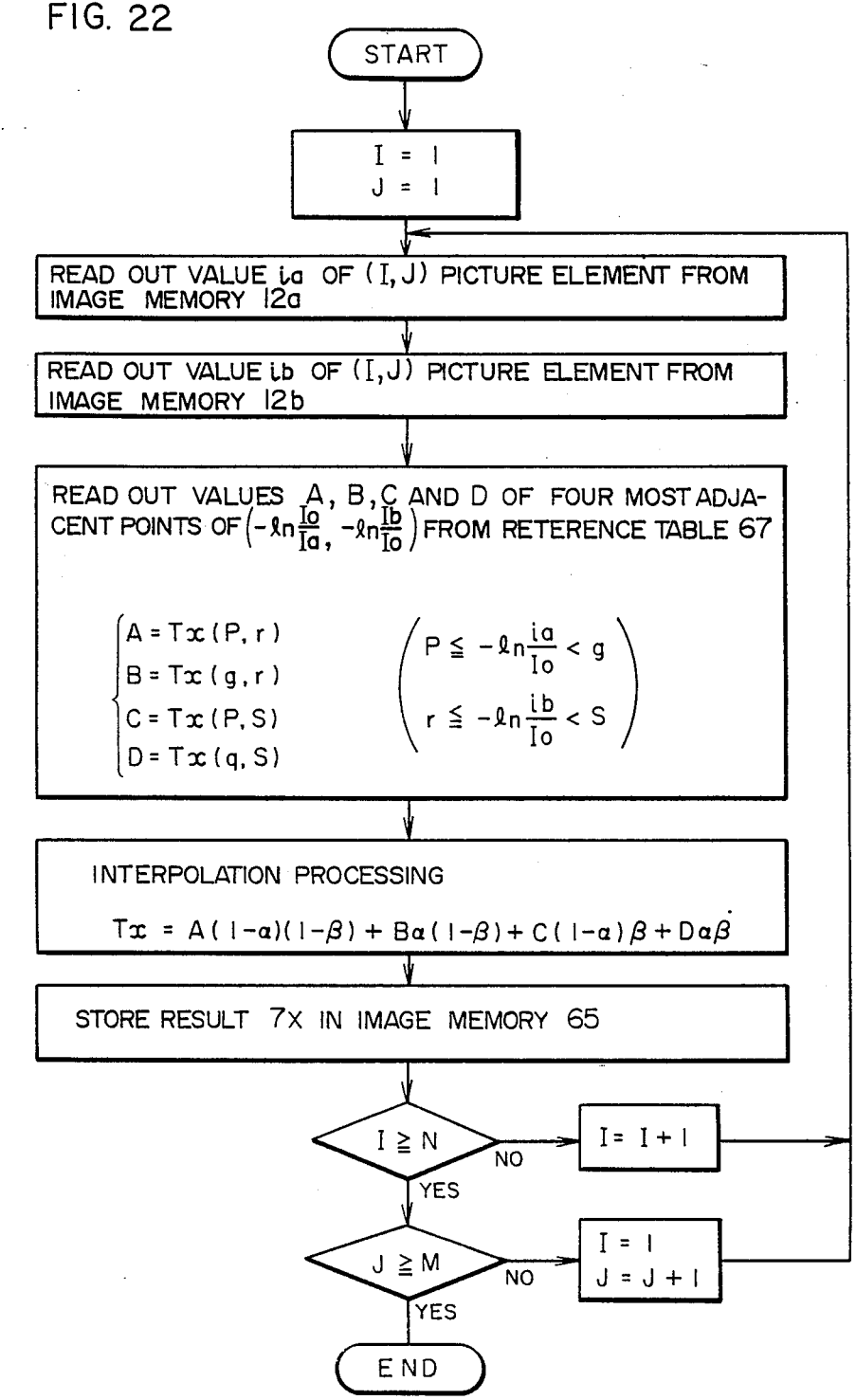
FIG. 22 is a flow chart showing the processing procedure performed in the image separation processing section of FIG. 15.
Figure 23:
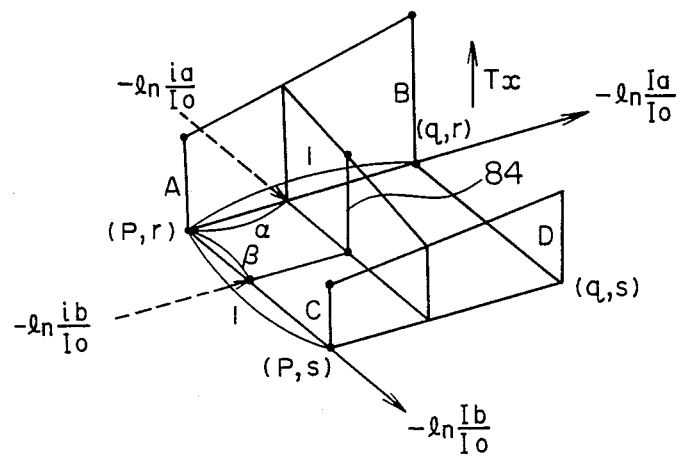
FIG. 23 is a view for explaining the interpolation technique of the numerical table of FIG. 21.

The processing procedure in the image separation processing section 66 is shown in the flowchart of FIG. 22. First, the values $i_a$ and $i_b$ of the corresponding picture elements are read out from the image memories 12a and 12b and $-\ln(i_a/Io)$ and $-\ln(i_b/Io)$ are calculated. The corresponding Tx is calculated by interpolating the values on the reference table 67. The interpolation is carried out as follows, for example. It is assumed that the values of four points most adjacent from a point at issue on the reference table are A, B, C and D as shown in FIG. 23. And, further assuming that the intervals of sampling points in a matrix shape recorded in the reference table are set at 1 and $\alpha$ and $\beta$ are set as shown in FIG. 23, the value of Tx can be obtained through a liner interpolation as follows.

$$Tx = A(1-\alpha)(1-\beta) + B\alpha(1-\beta) + C(1-\alpha)\beta + D\alpha\beta$$

The above processing is successively carried out for (N×M) picture elements on the imge memories 12a and 12b. By storing the results at the corresponding points on an image memory 65, an image of the solder of Pb is obtained.

A method of setting the numerical values on the reference table 67 will be explained. Since it is difficult to experimentally measure these numerical values, they are actually set through computer simulation. As a first step, the spectrum $\psi_{oa}(E)$ of the X-ray a(80) to be irradiated should be obtained. To this end, the spectrum of the X-ray source decided by the tube voltage $E_o$ is approximated using the theoretical equation of Kramers as follows.

$$\psi(E) = K(E_o - E) \tag{12}$$

where K is a constant, $E_o$ is the tube voltage and E is a photon energy. Thus, assuming that the X-ray absorption coefficient of w is $\mu_w(E)$ and the thickness of the filter is t, the spectrum of the X-ray a is expressed by $$\psi_{oa}(E) = \psi(E) \exp(-\mu_w(E)t) \tag{13}$$

As a second step, the transmission X-ray intensity Ia obtained after the irradiated X-ray $\psi_{oa}(E)$ has been transmitted through Pb of the thickness Tx and w of the thickness Ty is calculated for several sets of Tx and Ty as follows $$Ia = \int_0^\infty \psi_{oa}(E) \exp(-\mu_{Pb}(E)T_x - \mu_w(E)T_y)\, \alpha E \tag{14}$$

Figure 24A:
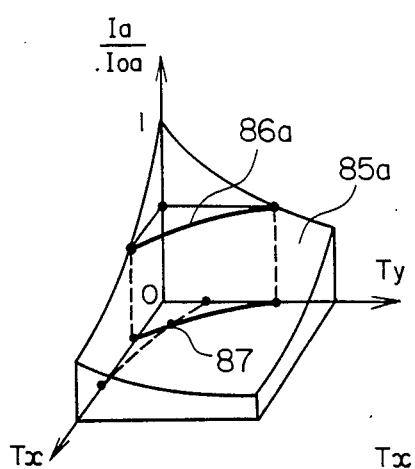
FIG. 24(a,b) is a view for explaining the method for setting the contents o the reference table by means of simulation.
Figure 24B:
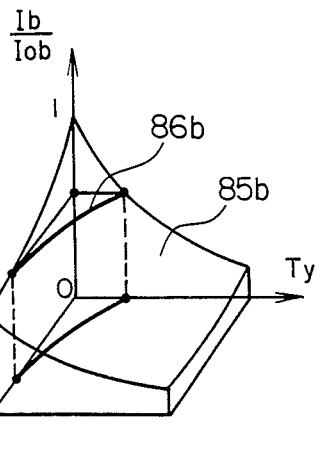

The computation by a computer is actually carried out as follows with the photon energy E divided into minute intervals $$Ia = \sum_E \psi_{oa}(E) \exp(-\mu_{Pb}(E)T_x - \mu_w(E)T_y)\Delta E \tag{15}$$

where $\mu_{Pb}(E)$ and $\mu_w(E)$ are the X-ray absorption coefficients of Pb and w, respectively. Now, if the ratio of the transmission X-ray intensity $I_a$ to the irradiated X-ray intensity $$I_{oa}\left(= \int_0^\infty \psi_{oa}(E)dE\right),$$

i.e. $I_a/I_{oa}$ is represented as a function of $T_x$ and $T_y$, the curved surface as shown in FIG. 24a is obtained. The curved surface 85b shown in FIG. 24b is obtained for the X-ray b in the same manner.

These curved surfaces as a function of $T_x$ and $T_y$ through the numerical computation by a computer may be obtained by dividing the $T_x$-$T_y$ plane into dots arranged in a matrix shape in $T_x$ and $T_y$ directions, calculating the values of $I_a/I_{oa}$ ($I_b/I_{ob}$) and connecting the values by lines to approximate the curved surface. As a third step, a set of $T_x$ and $T_y$ corresponding to a certain set of $I_a/I_{oa}$ and $I_b/I_{ob}$ are calculated from those two curved surfaces. The set of $T_x$ and $T_y$ corresponding to a certain $I_a/I_{oa}$ are present on a curve 86a in FIG. 24A while the set of $T_x$ and $T_y$ corresponding to a certain $I_b/I_{ob}$ are present on a curve 86b in FIG. 24B. These curves intersect at a point 87 on the $T_x$-$T_y$ plane. This point 87 represents only one set of $T_x$ and $T_y$ corresponding a certain set of $I_a$ and $I_b$. By carrying out the above three steps of computation (calculation) for several sets of $I_a$ and $I_b$ and registering the thus obtained values of $T_x$ on the reference table 67, the reference table 67 can be prepared. The above method of setting the numerical values on the reference table through numerical value computation, which carries out the simulation of X-ray transmission with the photon energy divided into minute intervals, can consider the quality change of the X-ray due to the transmission.

Through the procedure mentioned above, a solder image can be obtained in the image memory 65. By observing it displayed on e.g. a monitor, the soldering test can be made with high precision. Further, by inputting this image into a processor having a defect recognition algorithm, an automatic testing system for soldering effects can be constituted.

The first embodiment of separately detecting a soldering portion in accordance with the present invention, in which the X-ray is selected by simultaneously performing the tube voltage control and the filter exchange, has a comparatively high freedom of selecting the X-ray so that the irradiated X-ray can be easily made to have an optimum spectrum. Thus, a large difference in the values detected using two kinds of X-ray can be taken to enhance the separation accuracy.

Figure 25:
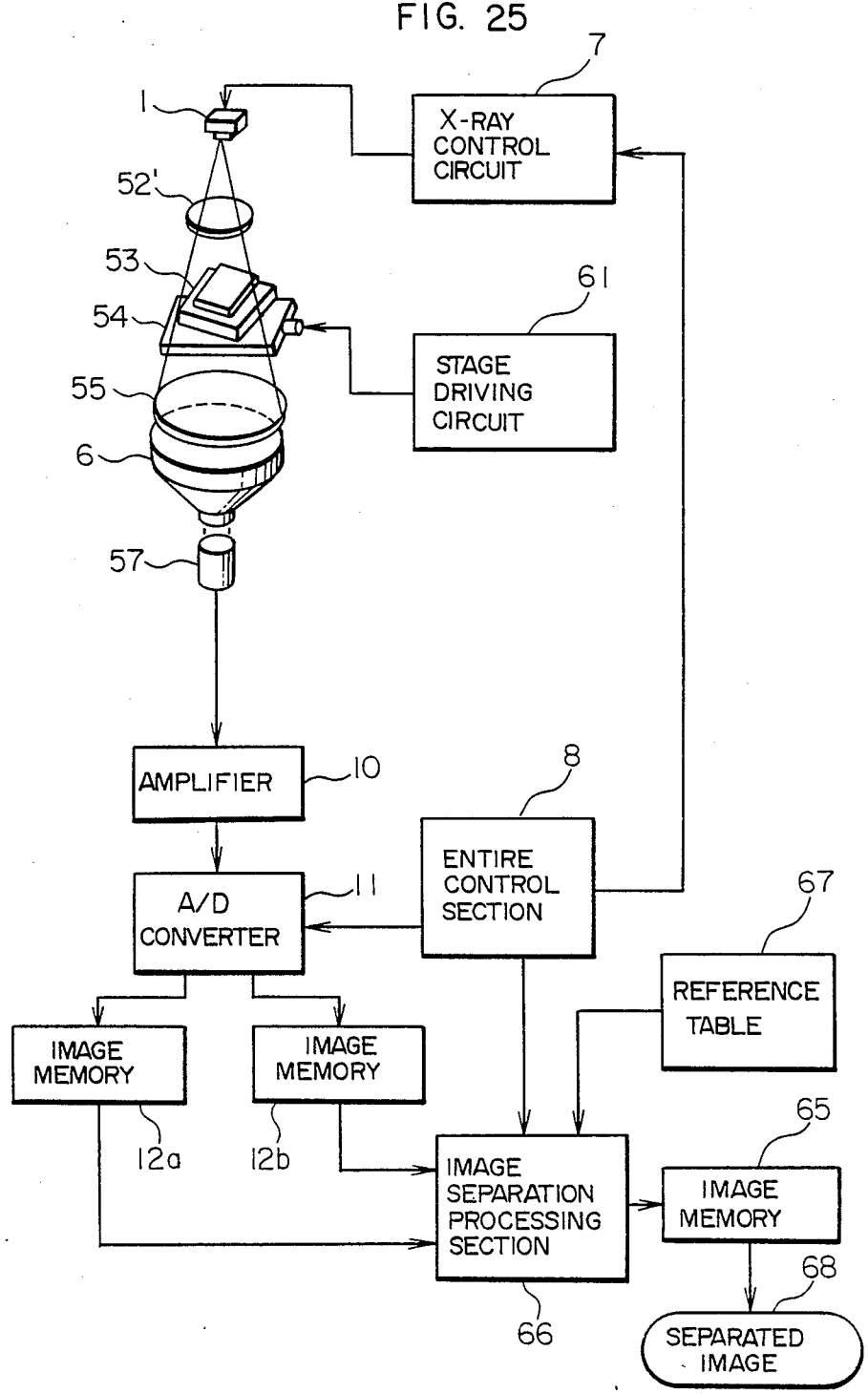
FIGS. 25, 26 and 27 are schematic block diagrams of further embodiments according to the present invention which are different from that of FIG. 15.

FIG. 25 shows a second embodiment of a device for separately detecting a solder portion in accordance with the present invention. This embodiment is the same as the first embodiment of FIG. 15 except that the filter exchange circuit 60 for a filter 52' is not provided. In this embodiment, the irradiated X-ray is selected only through the tube voltage control. The absence of a mechanical filter exchange mechanism advantageously simplify the structure of the device.

Figure 26:
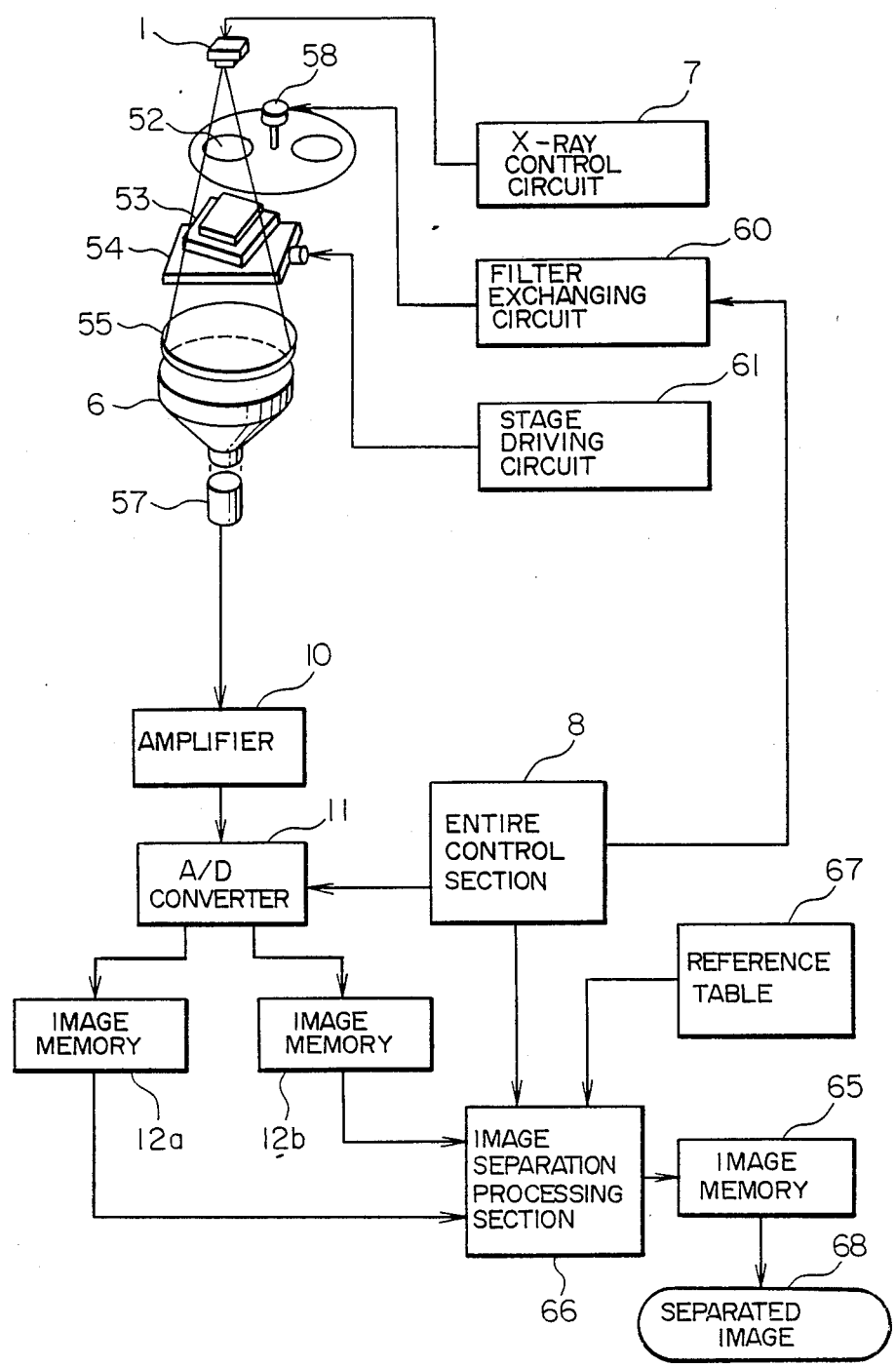

FIG. 26 shows a third embodiment of a device for separately detecting a solder portion in accordance with the present invention. This embodiment is the same as the first embodiment of FIG. 15 except that the X-ray is selected only by the filter 52 without changing the tube voltage by the X-ray control circuit 7. Unnecessity of changing the tube voltage permits the X-ray source to be operated in its steady state, and make it unnecessary to adjust the focussing point (which is required with the tube voltage change). Therefore, the stability and reproduction property of X-ray generation can be improved.

Figure 27:
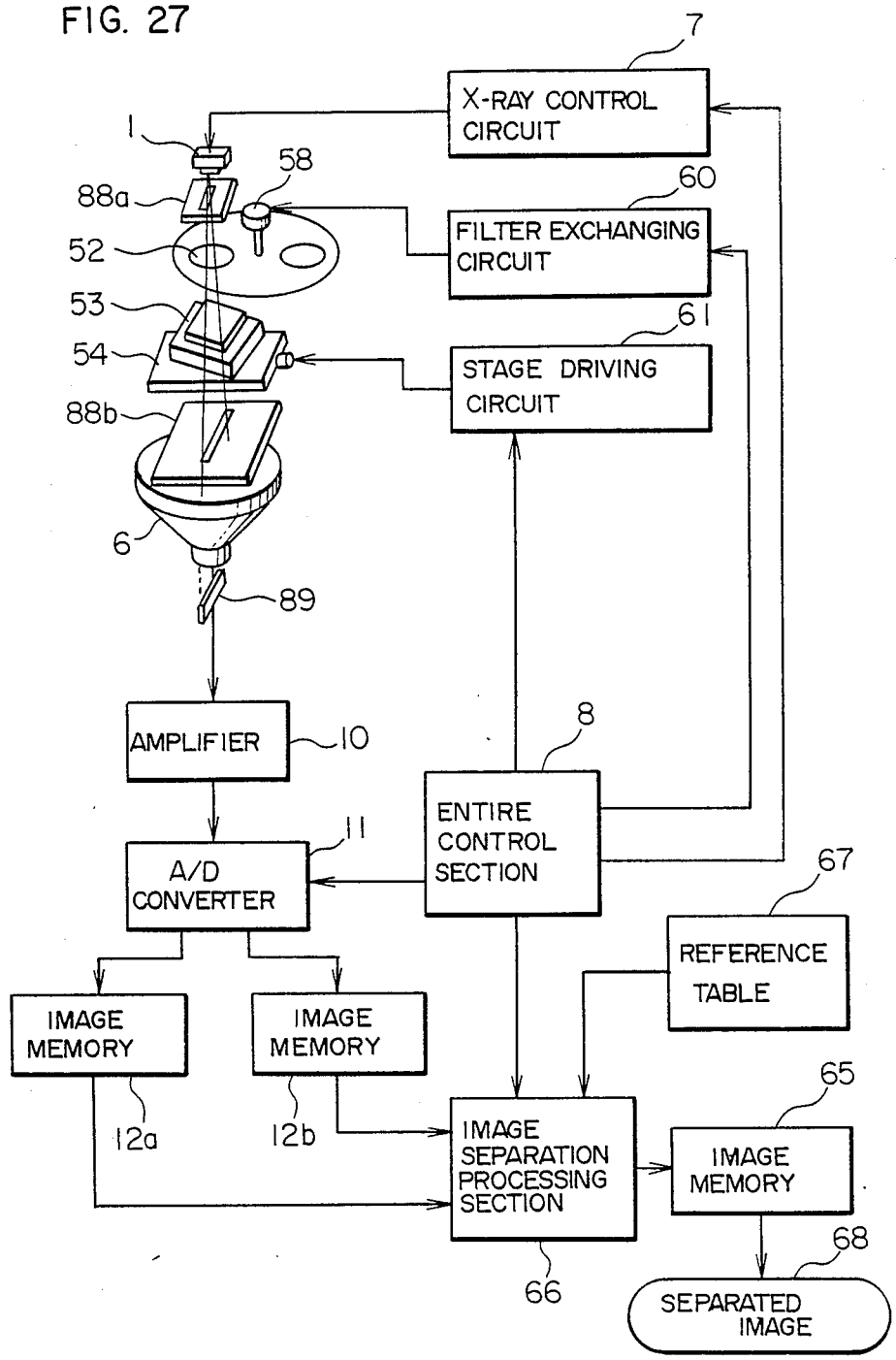

FIG. 27 shows a fourth embodiment of a device of separately detecting a soldering portion in accordance with the present invention. This embodiment is different from the first embodiment of FIG. 15 in that slits 88a and 88b are used in place of the X-ray grid 55 and a CCD line sensor 89 in the detector. The slits 88a and 88b are made of metal such as Pb so that they can intercept the X-ray. In this embodiment, the X-ray to be irradiated to the object 53 is limited to a thin band by the slit 88a and unnecessary X-ray incident to the detector is eliminated by the slit 88b so that the influence from the scattering X-ray can be greatly reduced, thereby permitting the high precision detection. In this embodiment, the object is scanned in the direction perpendicular to the slits 88a and 88b by the sample stage 54, and the image is detected in synchronization with the scanning by the CCD line sensor arranged in parallel to the slits 88a and 88b.

As explained above, in accordance with the present invention, an image of a specific substance can be separately detected with high accuracy from the X-ray transmission image in which the images of a plurality of substances are superposed. Since a specific portion of the X-ray transmission image can be selectively detected, the observation and testing can be made easy.

We claim:

1. A method for detecting with an X-ray imaging apparatus a defective portion of a plurality of solder connections of an object connected with said solder connections between an IC device and a multi-layer circuit board comprising the steps of:

exchanging by a filter exchanging means a lead plate filter used to filter a first X-ray having a first photon energy spectra fitted to said solder connections, and a wiring lead metal plate filter used to filter a second X-ray having a second photon energy spectra fitted to a wiring lead formed in the multi-layer circuit board;

irradiating the object with each of said first X-ray and said second X-ray at a predetermined angle perpendicular to a surface of the object, such that an X-ray transmission intensity signal (Ia) of the solder connections and an X-ray transmission intensity image signal (Ib) of the wiring leads are obtained;

detecting each of the X-ray transmission intensity image signals (Ia, Ib) of the object obtained by irradiating each of said first X-ray and said second X-ray to the object so that said intensity image signal (Ia) of the solder portions and said intensity image signal of the wiring lead (Ib) are superposed;

converting each of the X-ray transmission intensity image signals (Ia, Ib) from analog format to digital format;

storing to selected image memories each of the converted digital X-ray transmission intensity image signals (Ia, Ib); and extracting by an image separation processing means a thickness image ($T_x$) of the solder portions from the superposed images by processing values of said digital intensity image signals (Ia, Ib) for each of a plurality of picture elements (I, J) readout from each of the selected image memories over a predetermined area, the processing being accomplished by referring to a numerical value table indicating relations between transmission X-ray intensity values and values of image thicknesses (Tx) of the solder portions.

2. The method according to claim 1, wherein said transmission X-ray intensity values of the numerical value table are indicated by exponential values.

3. The method according to claim 2, wherein each of the values of image thicknesses (Tx) corresponding to said each of the picture elements (I,J) is calculated by linearly interpolating intensity values of points adjacent from said picture element recorded in said numerical value table.

4. An apparatus for detecting a defective portion of a plurality of solder connections of an object which is connected with the solder connections between an IC device and a multi-layer circuit board comprising:

an X-ray source having control means for controlling a tube voltage;

a filter exchanging means for exchanging a lead plate filter used to obtain a first X-ray having a first photon energy spectra fitted to said solder connections, and a wiring lead metal plate filter used to obtain a second X-ray having a second photon energy spectra fitted to a wiring lead formed in the multi-layer circuit board;

irradiating means for irradiating each of said first X-ray and said second X-ray to the object from a predetermined angle perpendicular to a surface of the object, such that an X-ray transmission intensity image signal (Ia) of the solder portions and an X-ray transmission intensity image signal (Ib) of the wiring lead ae obtained;

detecting means for detecting each of the X-ray transmission intensity image signals (Ia, Ib) of the object obtained by irradiating each of said first X-ray and said second X-ray to the object so that said intensity image signal (Ia) of the solder portions and said intensity image signal (Ib) of the wiring lead are superposed;

an A/D converter for converting from said each of the X-ray transmission intensity image signals (Ia, Ib) to digital X-ray transmission intensity image signals corresponding to a plurality of picture elements (I,J);

an image memory for storing each of the digital X-ray transmission intensity image signals obtained from said A/D converter;

a numerical value table indicating relations between the transmission X-ray intensity values and the thickness (Tx) of the solder portions; and, an image separation processing means for extracting a value representative of image thickness (Tx) of the solder portions from the superposed images by processing values of said digital intensity image signals (Ia, Ib) for each of the picture elements (I,J) readout from the image memory over a predetermined area by referring to said numerical value table.

5. The apparatus according to claim 4, wherein said transmission X-ray intensity values of the numerical value table are indicated by exponential values.

6. The apparatus according to claim 4, wherein said image separation processing means includes calculating means for calculating each of the values representative of image thickness (Tx) corresponding to said each of picture elements (I,J) by linearly interpolating the intensity values of points adjacent from said picture element recorded in said numerical value table.

* * * * *